United States Patent
Menke et al.

(10) Patent No.: US 10,345,263 B2
(45) Date of Patent: Jul. 9, 2019

(54) FILTER BLEEDING MEASUREMENT ARRANGEMENT AND TANK BLEEDING MEASUREMENT ARRANGEMENT

(71) Applicant: Dr. Ing. h.c. F. Porsche Aktiengesellschaft, Stuttgart (DE)

(72) Inventors: Andreas Menke, Vaihingen a.d.Enz/Enzweihingen (DE); Tobias Friedrich, Wimsheim (DE); Stefan Heinzel, Stuttgart (DE)

(73) Assignee: DR. ING. H.C. F. PORSCHE AKTIENGESELLSCHAFT, Stuttgart (DE)

(*) Notice: Subject to any disclaimer, the term of this patent is extended or adjusted under 35 U.S.C. 154(b) by 0 days.

(21) Appl. No.: 15/598,323

(22) Filed: May 18, 2017

(65) Prior Publication Data

US 2017/0336359 A1    Nov. 23, 2017

(30) Foreign Application Priority Data

May 20, 2016  (DE) .................. 10 2016 109 271

(51) Int. Cl.
    *G01N 27/62*    (2006.01)
(52) U.S. Cl.
    CPC .................. *G01N 27/626* (2013.01)

(58) Field of Classification Search
    CPC ................................... G01N 27/626
    See application file for complete search history.

(56) References Cited

U.S. PATENT DOCUMENTS

| | | |
|---|---|---|
| 5,073,753 A | 12/1991 | Collings et al. |
| 6,575,012 B1 | 6/2003 | Aronsson et al. |
| 2014/0102178 A1 | 4/2014 | Menke et al. |
| 2015/0153291 A1 | 6/2015 | Harms et al. |
| 2015/0240772 A1 | 8/2015 | Yamamoto et al. |

FOREIGN PATENT DOCUMENTS

| | | |
|---|---|---|
| DE | 102008011453 A1 | 9/2009 |
| DE | 102012010241 A1 | 11/2013 |
| DE | 102012109842 A1 | 5/2014 |

*Primary Examiner* — Samuel P Siefke
(74) *Attorney, Agent, or Firm* — Leydig, Voit & Mayer, Ltd.

(57) ABSTRACT

A filter bleeding measurement arrangement for the pressure-neutral determination of the fuel vapor emissions of a fuel vapor filter includes a flame ionization detector with a gas inlet and a gas outlet, and a measurement adapter including a measurement connection for connection of the fuel vapor filter, a separate detector connection for connection of the flame ionization detector, and an air inlet fluidically connected to an external atmosphere.

15 Claims, 2 Drawing Sheets

FILTER BLEEDING MEASUREMENT ARRANGEMENT AND TANK BLEEDING MEASUREMENT ARRANGEMENT

CROSS REFERENCE TO RELATED APPLICATIONS

This application claims benefit to German Patent Application No. DE 10 2016 109 271.1, filed May 20, 2016, which is incorporated by reference herein.

FIELD

The invention relates to a filter bleeding measurement arrangement and to a tank bleeding measurement arrangement comprising a filter bleeding measurement arrangement for the quantitative determination of hydrocarbon emissions or bleeding emissions from the fuel vapor filter.

BACKGROUND

The emission of hydrocarbons from motor vehicles operated with fossil fuels is subject to legal restrictions. In particular, the gaseous hydrocarbon emissions from the tank arrangement of motor vehicles, also called bleeding emissions, are subject to restrictions and therefore have to be able to be precisely identified in the laboratory. In this connection, a differentiation is intended to be made between the bleeding emissions which the tank arrangement has because of leakages and permeation, and the bleeding emissions which the fuel vapor filter connected to the venting connection of the fuel tank outputs through its connection to the environment.

DE 10 2012 010 241 A1 discloses a measurement arrangement in which fuel vapor is supplied by a pump to a fuel vapor filter which is arranged in a hot cabinet.

DE 10 2012 1098421 discloses a method for determining the buffer effect of a fuel vapor filter for hydrocarbon-containing fuels.

SUMMARY

In an embodiment, the present invention provides a filter bleeding measurement arrangement for pressure-neutral determination of fuel vapor emissions of a fuel vapor filter. The filter bleeding measurement arrangement includes a flame ionization detector with a gas inlet and a gas outlet, and a measurement adapter including a measurement connection for connection of the fuel vapor filter, a separate detector connection for connection of the flame ionization detector, and an air inlet fluidically connected to an external atmosphere.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
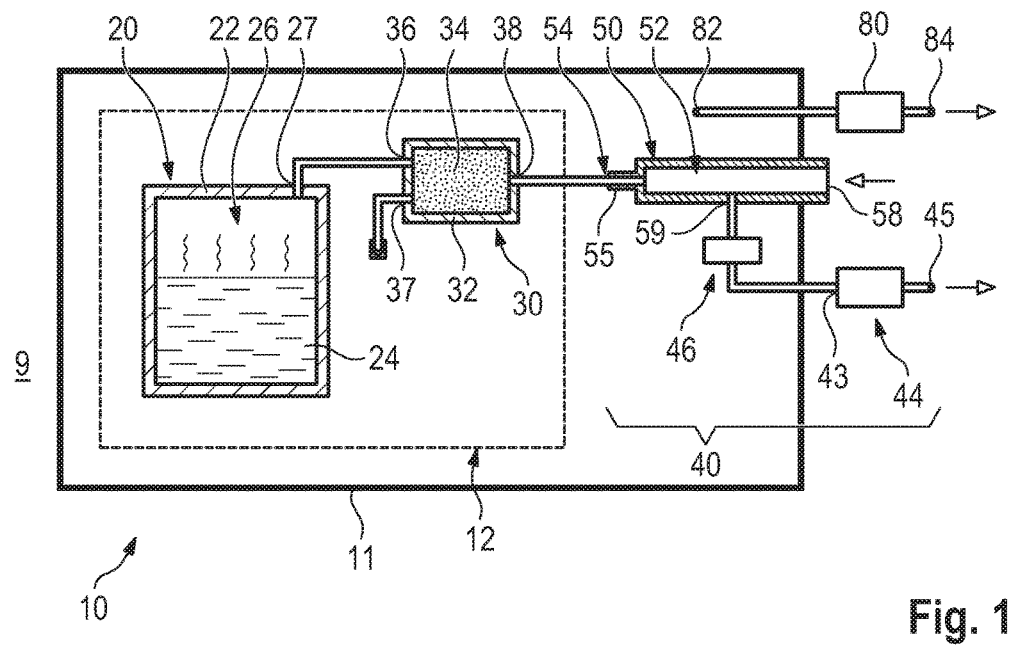
FIG. 1 shows a schematic illustration of a tank bleeding measurement arrangement with a first embodiment of a filter bleeding measurement arrangement, including a measurement adapter.

A filter bleeding measurement arrangement is described herein by way of which a pressureless measurement of the bleeding emissions of fuel vapor filter is possible. A tank bleeding measurement arrangement is described herein which permits a differentiated measurement of the hydrocarbon emissions of the entire tank arrangement.

A filter bleeding measurement arrangement according to an embodiment of the invention has a flame ionization detector and a measurement adapter for the pressure-neutral determination of the hydrocarbon emissions for a fuel vapor filter. The flame ionization detector optionally continuously sucks up the measurement gas through its gas inlet and outputs said measurement gas via its gas outlet to the atmosphere. The flame ionization detector sucks up a not inconsiderable quantity of measurement gas via its gas inlet, and therefore it cannot be connected directly to the ventilating connection of the fuel vapor filter without having a direct influence on the measurement result.

The filter bleeding measurement arrangement therefore has a measurement adapter which has a measurement connection for the connection of the ventilating connection of the fuel vapor filter, a separate detector connection for the connection of the flame ionization detector and a separate air inlet which is fluidically connected to the vapor-free atmosphere. The measurement adapter therefore has three connections and permits a virtually pressure-free measurement of the fuel vapor emissions of the fuel vapor filter. The air inlet of the measurement adapter has a low flow resistance in relation to the flow resistance of the measurement connection. It is thereby ensured that most of the quantity of gas sucked up by the flame ionization detector, namely up to more than 90%, flows through the air inlet, whereas only a fraction of less than 10% flows through the measurement connection into the measurement adapter. In this way, only the hydrocarbon vapors output passively and in a virtually pressure-free manner by the connected fuel vapor filter, via its venting, are detected by the flame ionization detector. If a negative pressure arises in the connected fuel vapor filter, for example caused by a reduction in the ambient temperature, the fuel vapor filter exclusively sucks up vapor-free atmosphere out of the measurement adapter, as would also correspond to reality.

Such a filter bleeding measurement arrangement permits precise and pressure-free measurement of the filter bleeding can be produced with relatively simple means.

The measurement adapter preferably has a tubular adapter housing which is circular in cross section with a constant tube inside diameter D1 and a tube length L. The quotient L/D1 of tube length L and tube inside diameter D1 is between 5.0 and 15.0, is preferably between 7.0 and 10.0 and is particularly preferably at approximately 8.6. The measurement connection and the air inlet are preferably respectively provided at the two longitudinal ends of the adapter housing. The detector connection is preferably provided approximately in the center of the longitudinal extent of the adapter housing. The interior of the adapter housing forms an elongate settling volume in which the fuel vapors coming from the fuel vapor filter and the vapor-free atmospheric air flowing through the air inlet are optionally mixed. This gas mixture generated in this manner then flows to the flame ionization detector.

According to a preferred embodiment of the invention, the measurement adapter has a tubular adapter housing with a constant housing cross section Q1 and an inlet tube which has the measurement connection and a likewise constant inlet tube cross section Q2. In the present case, "cross section" is always understood as meaning the cross-sectional area. The inlet tube opens into the adapter housing. Both the inlet tube and the adapter housing can basically have any desired cross-sectional shape, for example a polygonal shape, but are preferably of circular design in cross section.

The cross section Q2 of the inlet tube is considerably smaller than the cross section Q1 of the housing. The quotient Q1/Q2 of the housing cross section and the inlet tube cross section is between 30 and 50, preferably between 35 and 45, and particularly preferably in the region of approximately 40. The flow speed of the gas flowing through the measurement connection of the measurement adapter is therefore also approximately at $\frac{1}{30}$ to $\frac{1}{50}$ of the flow speed of the fuel-vapor-free atmospheric air flowing through the air inlet, and therefore the negative pressure present on the outside of the measurement adapter measurement connection is negligibly small. The emission of the connected fuel vapor filter is thereby measured in a virtually pressure-free manner.

The measurement adapter preferably has a tubular adapter housing with a constant cross section Q1, wherein the cross section Q3 of the air inlet is at least 0.5 times the tube cross section Q1 of the adapter housing. The cross section Q3 of the air inlet particularly preferably corresponds approximately to 0.8 times the cross section Q1 of the tubular adapter housing. The fuel-vapor-free atmospheric air therefore flows into the adapter housing virtually without a significant loss of pressure.

According to a particularly preferred embodiment of the measurement arrangement, the outlet opening is arranged approximately in the center of the tube length of the tubular adapter housing.

The tubular adapter housing is preferably shaped in such a manner that the outlet opening which leads to the detector connection is arranged at the lowest point of the tubular adapter housing. It is further ensured that even hydrocarbon condensate forming in the adapter housing ultimately passes via the outlet opening and the detector connection to the flame ionization detector and is quantitatively detected there. The adapter housing is preferably of arcuate design, wherein the outlet opening is arranged approximately in the arc center which constitutes the lowest point of the adapter housing.

According to a preferred embodiment, a homogenization container is provided which is connected downstream to the detector connection, i.e. is arranged fluidically between the detector connection and the flame ionization detector connected to the homogenization container. The homogenization container serves to homogenize the gas mixture mixed in the measurement adapter. Since the flame ionization detector has a certain measurement inertia, the homogenization permits a precise quantitative determination of the fuel vapor emissions of the fuel vapor filter.

A tank bleeding measurement arrangement is described herein that can be provided for the differentiated determination of the fuel vapor emissions of the fuel tank, on the one hand, and of the fuel vapor filter assigned to the fuel tank, on the other hand.

A tank bleeding measurement arrangement according to an embodiment has a filter bleeding measurement arrangement as described above, wherein the measurement adapter air inlet and the flame ionization detector outlet are both fluidically connected in each case to the fuel-vapor-free atmosphere.

The tank bleeding measurement arrangement has a test stand chamber in which the fuel tank and the fuel vapor filter assigned fluidically to the fuel tank are arranged. The fuel tank has a venting connection which is fluidically connected to a tank connection of the fuel vapor filter. The fuel vapor filter furthermore has a measurement connection which is fluidically connected to the measurement connection of the measurement adapter. Finally, the tank bleeding measurement arrangement has a second flame ionization detector, the gas inlet of which opens into the interior of the test stand chamber.

This provides a tank bleeding measurement arrangement with which both the filter bleeding emissions and the tank bleeding emissions can be measured at the same time, independently of one another and differentiated from one another.

Alternatively, provision can be made to provide a single flame ionization detector which determines the emissions of the fuel vapor filter and of the fuel tank in an alternating manner, for example in a regularly alternating manner. For this purpose, a fluid valve which can be appropriately switched over would be provided. However, the two emission categories could not simultaneously be determined here within the narrower sense.

FIG. 1 shows substantially schematically a tank bleeding measurement arrangement 10 which serves for the differentiated determination of the fuel vapor emissions due to permeation and micro leakages of a tank arrangement 12 and of the fuel vapors emerging from the ventilating connection 38 of the fuel vapor filter 30 of the tank arrangement 12.

The tank bleeding measurement arrangement 10 has a test stand chamber 11 which separates the interior of the chamber 11 in a substantially gas-tight manner from the fuel-vapor-free atmosphere 9 surrounding a chamber 11. The tank arrangement 12 is the measurement object and essentially consists of a fuel tank 20 and a fuel vapor filter 30 which is assigned to the latter and is fluidically connected to a venting connection 27 of the fuel tank 20.

The fuel tank 20 has a tank container 22 in which liquid fuel 24, for example gasoline, is stored. Fuels and in particular gasoline are volatile, and therefore fuel vapors 26 always arise and are present within the tank container 22 and escape through the venting connection 27 of the tank 20 in the event of a rise in temperature. The fuel vapors 26 are supplied through the venting connection 27 to a tank connection 36 of the fuel vapor filter 30. The fuel vapor filter 30 essentially consists of a filter container 32 which is filled with a filter filling 34, for example with activated carbon. The fuel vapor filter 30 has a fluidic motor connection 37 which is closed for the measurement operation, and a ventilating and measurement connection 38 which is fluidically connected to a filter bleeding measurement arrangement 40.

Upon expansion of the fuel volume within the tank container 22, the filter filling 34 is loaded with the fuel vapor, and therefore substantially fuel-vapor-free gas flows out of the ventilating and measurement connection 38 of the fuel vapor filter 30. However, this does not apply, for example, if the filter filling 34 is already saturated with fuel vapor or else the absolute capacity of the filter filling 34 changes due to changes in temperature. In these cases, in particular while the tank arrangement 12 is not in operation, for example if the motor vehicle concerned is not in operation, it is entirely possible for hydrocarbon-containing fuel vapor to emerge out of the ventilating and measurement connection 38. Furthermore, the tank arrangement 12 moreover has micro leakages in practice, i.e. is not absolutely leak proof, since hydrocarbons are sometimes molecularly very small and absolute tightness cannot be realized at acceptable costs.

The present tank bleeding measurement arrangement 10 now makes it possible to determine the two bleeding categories separately from each other precisely and simultaneously. An important additional requirement here is that the filter bleeding emissions which emerge from the ventilating and measurement connection 38 are determined in a pressure-free manner. The filter bleeding measurement arrangement 40 connected to the ventilating and measurement connection 38 does therefore not generate any significant positive or negative pressure with respect to the atmospheric air pressure that could influence the measurement result.

Figure 2:
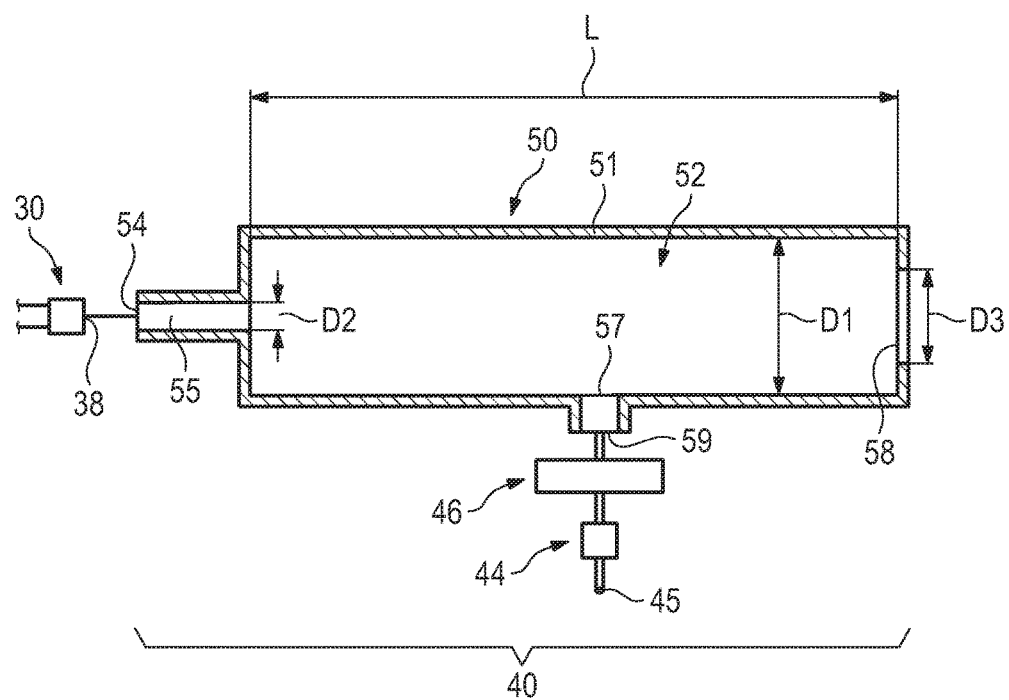
FIG. 2 shows the filter bleeding measurement arrangement of FIG. 1 including the measurement adapter in a longitudinal section view.

A first embodiment of a filter bleeding measurement arrangement 40 is illustrated in detail in FIG. 2. The filter bleeding measurement arrangement 40 essentially consists of three elements, namely the measurement adaptor 50 lying in a horizontal plane, the homogenization container 46 and the first flame ionization detector 44.

The measurement adapter 50 has a measurement connection 54 which is fluidically connected to the ventilating and measurement connection 38 of the fuel vapor filter 30. An inlet tube 55 which is circular in cross section and has an inside diameter D2 is connected to the measurement connection 54. The inlet tube 55 opens into a tubular adapter housing 51 which is preferably circular in cross section and has an inside diameter D1 and an inner length L. The ratio of the length L of the adapter housing 51 to its inside diameter D1 is approximately 8.6. The inner length L is approximately 300 mm and the inside diameter D1 is approximately 35 mm. The inside diameter D2 of the inlet tube 55 is approximately 5 mm, and therefore the ratio of the inner cross section Q1 of the adapter housing 51 to the inner cross section Q2 of the inlet tube 55 is approximately 49. The other longitudinal end of the adapter housing 51 has an air inlet 58 which has an opening diameter D3 of approximately 31 mm. Fuel-vapor-free air flows out of the atmosphere 9 through the air inlet 58 into the interior of the adapter housing 51, the interior defining a settling volume 52.

Approximately in the center of the longitudinal extent of the adapter housing 51, an outlet opening 57 is provided at the lowest point in the wall, said outlet opening fluidically into a detector connection 59 of the measurement adapter 50. The detector connection 59 is fluidically connected to a homogenization container 46 in which the fuel vapor and air mixture is homogeneously mixed together. The homogenization container has a volume of approx. 1.5 L. The homogenization container 46 is illustrated in more detail in FIG. 3. It is a cup-shaped housing body 70 which has a tangential gas inlet 72 on the inside of its one longitudinal end and a gas outlet 74 at its other longitudinal end. The gas outlet 74 of the homogenization container 46 is fluidically connected to the gas inlet 43 of the first flame ionization detector 44, the detector outlet 45 of which opens into the atmosphere 9.

The tank bleeding measurement arrangement 10 has a second flame ionization detector 80, the gas inlet 82 of which opens into the interior of the measurement stand chamber 11 and the detector gas outlet 84 of which is arranged in the atmosphere. The second flame ionization detector 80 is used to measure the tank bleeding emissions, namely the hydrocarbon emissions because of leakages of the tank arrangement 12.

Figure 3:
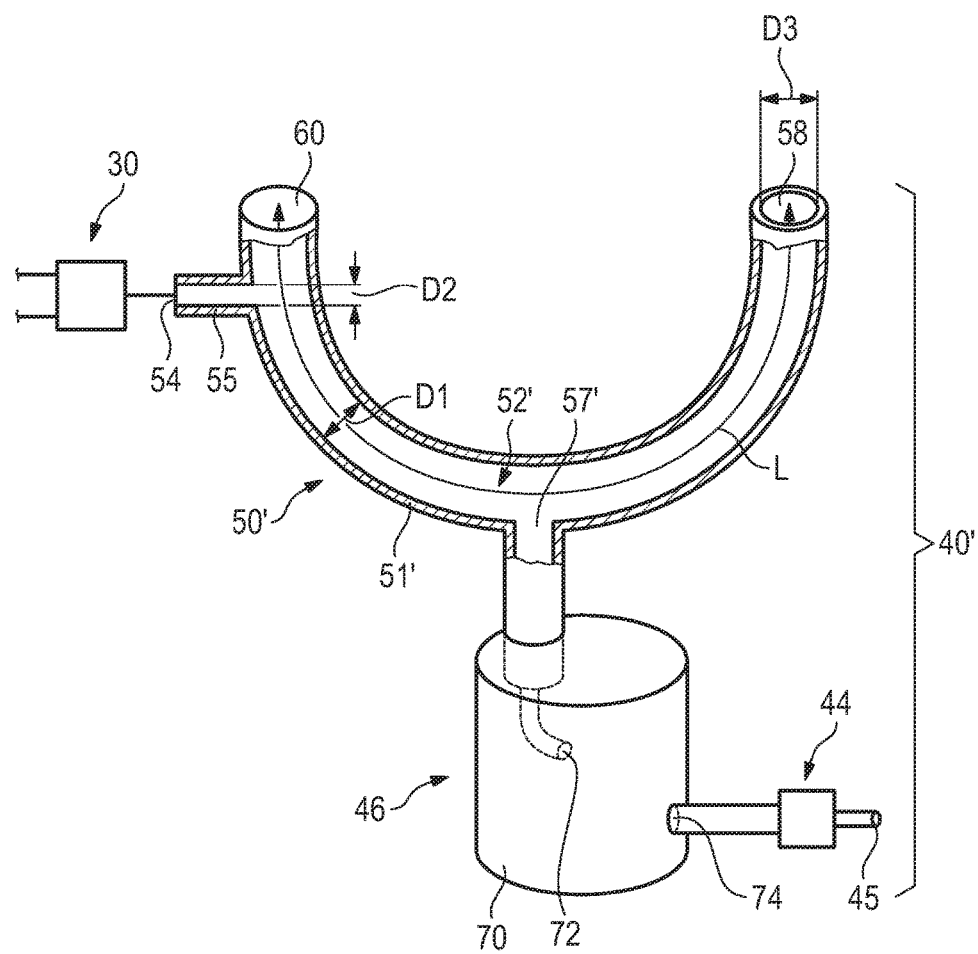
FIG. 3 shows a second embodiment of a filter bleeding measurement arrangement in partial longitudinal section view.

FIG. 3 illustrates a second exemplary embodiment of a filter bleeding measurement arrangement 40'. In contrast to the exemplary embodiment illustrated in FIG. 2, the filter bleeding measurement arrangement 40' of FIG. 3 has a measurement adapter 50' with an adapter housing 51' which has, for example, a semicircular arc and a correspondingly arcuate settling volume 52'. The arcuate adapter housing 51' stands in a vertical plane and the two semicircular ends lie in the same horizontal plane. The outlet opening 57' lies at the lowest point of the settling volume 52'.

In this embodiment, the geostatic height between outlet opening 57' and air inlet opening 58' ensures that all of the filter bleeding hydrocarbons pass into the settling container 46'. In addition to the U shape just described, a further embodiment in a V shape is conceivable.

A further embodiment presents a cylinder shape.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:

1. A filter bleeding measurement arrangement for pressure-neutral determination of fuel vapor emissions of a fuel vapor filter, the filter bleeding measurement arrangement comprising:
    a flame ionization detector including a gas inlet and a gas outlet; and
    a measurement adapter including:
        a measurement connection configured to connect to the fuel vapor filter, the measurement connection having a first cross section providing a first flow resistance,
        a separate detector connection configured to connect to the gas inlet of the flame ionization detector, and
        an air inlet fluidically connected to an external atmosphere, the air inlet having a second cross section providing a second flow resistance,
    wherein the second flow resistance is less than the first flow resistance.

2. The filter bleeding measurement arrangement as claimed in claim 1, wherein the measurement adapter further includes a tubular adapter housing having a constant tube inside diameter and a tube length, wherein the quotient of the length and the inside diameter is between 5.0 and 15.0.

3. The filter bleeding measurement arrangement as claimed in claim 1, wherein the measurement adapter further includes a tubular adapter housing having a constant housing cross section and an inlet tube,
wherein the inlet tube includes the measurement connection, has an inlet tube cross section, and opens into the tubular adapter housing, and
wherein the quotient of the housing cross section and the inlet tube cross section is between 30.0 and 50.0.

4. The filter bleeding measurement arrangement as claimed in claim 1, wherein the measurement adapter further includes a tubular adapter housing having a constant third cross section, and
wherein the second cross section is at least 0.5 times the third cross section.

5. The filter bleeding measurement arrangement as claimed in claim 1, wherein the measurement adapter further includes a tubular adapter housing having a tube length, wherein the tubular adapter housing has an outlet opening which leads to the detector connection, and wherein the outlet opening is arranged approximately at a center of the tube length.

6. The filter bleeding measurement arrangement as claimed in claim 1, wherein the measurement adapter further includes a tubular adapter housing, wherein the tubular adapter housing has an arcuate profile and includes an outlet opening which leads to the detector connection, wherein the tubular adapter housing is shaped in such a manner that the outlet opening is arranged at a lowest point of the tubular adapter housing.

7. The filter bleeding measurement arrangement as claimed in claim 1, further comprising a separate homogenization container provided fluidically between the detector connection and the flame ionization detector.

8. The filter bleeding measurement arrangement as claimed in claim 1, wherein a ratio of the second cross section to the first cross section is between 15:1 and 40:1.

9. The filter bleeding measurement arrangement as claimed in claim 7, wherein the separate homogenization container includes a housing body having a first longitudinal end, a second longitudinal end, a gas inlet at the first longitudinal end that is connected to the detector connection of the measurement adapter, and a gas outlet at the second longitudinal end that is connected to the gas inlet of the flame ionization detector.

10. The filter bleeding measurement arrangement as claimed in claim 2, wherein the quotient of the length and the inside diameter is between 7.0 and 10.0.

11. The filter bleeding measurement arrangement as claimed in claim 2, wherein the quotient of the length and the inside diameter is 8.6.

12. The filter bleeding measurement arrangement as claimed in claim 3, wherein the quotient of the housing cross section and the inlet tube cross section is between 35 and 45.

13. The filter bleeding measurement arrangement as claimed in claim 3, wherein the quotient of the housing cross section and the inlet tube cross section is 40.

14. The filter bleeding measurement arrangement as claimed in claim 4, wherein a cross section of the air inlet is 0.8 times the cross section of the tubular adapter housing.

15. The filter bleeding measurement arrangement as claimed in claim 1, wherein the measurement adapter further includes a tubular adapter housing having a constant tube inside diameter and a tube length,
wherein the second cross section is at least 0.5 times the tube inside diameter,
wherein a quotient of the tube length and the tube inside diameter is between 5.0 and 15.0, and
wherein a quotient of the tube inside diameter and the first cross section is between 30 and 50.

* * * * *